(12) United States Patent
Shim et al.

(10) Patent No.: US 11,051,762 B2
(45) Date of Patent: Jul. 6, 2021

(54) ELECTRONIC DEVICE

(71) Applicant: LG ELECTRONICS INC., Seoul (KR)

(72) Inventors: Hongjo Shim, Seoul (KR); Hyunok Lee, Seoul (KR); Yoonwoo Lee, Seoul (KR); Seonghyok Kim, Seoul (KR); Mihyun Park, Seoul (KR); Hyunwoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 392 days.

(21) Appl. No.: 15/754,841

(22) PCT Filed: Jan. 4, 2016

(86) PCT No.: PCT/KR2016/000016
§ 371 (c)(1),
(2) Date: Feb. 23, 2018

(87) PCT Pub. No.: WO2017/034099
PCT Pub. Date: Mar. 2, 2017

(65) Prior Publication Data
US 2018/0242915 A1 Aug. 30, 2018

(30) Foreign Application Priority Data

Aug. 25, 2015 (KR) .................. 10-2015-0119406

(51) Int. Cl.
*A61B 5/02* (2006.01)
*A61B 5/00* (2006.01)
(Continued)

(52) U.S. Cl.
CPC .............. *A61B 5/6898* (2013.01); *A61B 5/01* (2013.01); *A61B 5/02055* (2013.01);
(Continued)

(58) Field of Classification Search
CPC . A61B 5/6898; A61B 5/02055; G06F 1/1626; G06F 1/1684; H05K 1/183
See application file for complete search history.

(56) References Cited

U.S. PATENT DOCUMENTS 6,320,450 B1 * 11/2001 Lee .......................... G01J 5/16
327/513
2009/0068384 A1 * 3/2009 Seth .................. B32B 17/10055
428/34
(Continued)

FOREIGN PATENT DOCUMENTS

| JP | 2013-58864 A | 3/2013 |
| KR | 10-2005-0029782 A | 3/2005 |
| KR | 10-2012-0084792 A | 7/2012 |

*Primary Examiner* — Eric D. Bertram
(74) *Attorney, Agent, or Firm* — Birch, Stewart, Kolasch & Birch, LLP

(57) ABSTRACT

An electronic device is disclosed. The electronic device includes a case and a battery cover forming an appearance of the electronic device and a printed circuit board mounted inside the case and provided with electronic elements. A measurement sensor is mounted on at least a portion of the printed circuit board. One surface of a recess of the printed circuit board, on which the measurement sensor is mounted, is formed at a different height from other portion of the printed circuit board in a thickness direction of the electronic device. The recess, on which the measurement sensor is mounted, is thinner than the other portion and is spaced apart from the other portion, and thus the electronic device can more accurately measure a body temperature of a user.

16 Claims, 16 Drawing Sheets

(51) Int. Cl.
*H04M 1/02* (2006.01)
*H05K 3/46* (2006.01)
*G06F 1/16* (2006.01)
*H05K 1/02* (2006.01)
*A61B 5/01* (2006.01)
*A61B 5/0205* (2006.01)
*A61B 5/024* (2006.01)
*H05K 1/18* (2006.01)
*A61B 5/0255* (2006.01)
*G06F 3/041* (2006.01)

(52) U.S. Cl.
CPC ........ *A61B 5/02438* (2013.01); *G06F 1/1626* (2013.01); *G06F 1/1635* (2013.01); *G06F 1/1658* (2013.01); *G06F 1/1684* (2013.01); *H04M 1/0277* (2013.01); *H05K 1/0206* (2013.01); *H05K 1/183* (2013.01); *H05K 3/4697* (2013.01); *A61B 5/0075* (2013.01); *A61B 5/0255* (2013.01); *A61B 2562/0238* (2013.01); *A61B 2562/0276* (2013.01); *A61B 2562/063* (2013.01); *G06F 3/041* (2013.01); *G06F 2203/011* (2013.01); *H04M 1/0262* (2013.01); *H04M 2250/12* (2013.01); *H05K 2201/096* (2013.01); *H05K 2201/10151* (2013.01); *H05K 2201/10219* (2013.01)

(56) References Cited

U.S. PATENT DOCUMENTS

| | | | |
|---|---|---|---|
| 2009/0244709 A1* | 10/2009 | Suzuki | C03C 1/008 359/601 |
| 2012/0242588 A1* | 9/2012 | Myers | G06F 1/1637 345/173 |
| 2014/0275845 A1* | 9/2014 | Eagon | A61B 5/6826 600/301 |
| 2014/0275852 A1* | 9/2014 | Hong | A61B 5/0205 600/301 |
| 2015/0229750 A1 | 8/2015 | Zhou et al. | |
| 2015/0257664 A1* | 9/2015 | Esposito | A61B 5/02444 600/500 |
| 2016/0183813 A1* | 6/2016 | Naima | A61B 5/02416 600/479 |

* cited by examiner (a)

(b)

(c)

(d)

(a)

(b)

(a)

(b)

(a)

(b)

ELECTRONIC DEVICE

CROSS REFERENCE TO RELATED APPLICATIONS

This application is the National Phase of PCT International Application No. PCT/KR2016/000016, filed on Jan. 4, 2016, which claims priority under 35 U.S.C. 119(a) to Patent Application No. 10-2015-0119406, filed in Republic of Korea on Aug. 25, 2015, all of which are hereby expressly incorporated by reference into the present application.

TECHNICAL FIELD

The present disclosure relates to an electronic device, and more particularly to an electronic device in which a recess provided with a measurement sensor is thinner than other portion and is spaced apart from the other portion.

BACKGROUND ART

Terminals may be generally classified into mobile/portable terminals and stationary terminals based on a mobility. The mobile terminals may also be classified into handheld terminals and vehicle mounted terminals depending on whether or not a user can directly carry the terminal.

Mobile terminals have increasingly more functions. Examples of the functions include data and voice communications, taking pictures and videos with a camera, recording audio, playing music files using a speaker system, and displaying images and video on a display. Some mobile terminals include additional functionality which supports game playing, while other terminals are configured as multimedia players. More recently, the mobile terminals have been configured to receive broadcast and multicast signals which permit viewing of content such as videos and television programs.

As the mobile terminals have increasingly more functions, the mobile terminals have been implemented as multimedia players of multiple functions having taking pictures and videos, playing music files or video, game playing, receiving broadcast, and the like.

Efforts are ongoing to support and increase the functionality of mobile terminals. Such efforts include software and hardware improvements, as well as changes and improvements in the structural components.

A study on wearable electronic devices the user wears is being recently carried out. For example, an attempt has been made to study glass wearable electronic devices, watch wearable electronic devices, and the like.

Because the wearable electronic device has to arrange necessary electronic components in a limited space while satisfying design requirements, a need for an optimum design of the wearable electronic device is increasing.

DISCLOSURE

Technical Problem

An object of the present disclosure is to address the above-described and other problems. Another object of the present disclosure is to provide an electronic device which is configured such that a recess provided with a measurement sensor is thinner than other portion and is spaced apart from the other portion, and thus can more accurately measure a body temperature of a user.

Technical Solution

In one aspect of the present disclosure, there is provided an electronic device comprising a case and a battery cover forming an appearance of the electronic device, and a printed circuit board mounted inside the case and provided with electronic elements, wherein a measurement sensor is mounted on at least a portion of the printed circuit board, wherein one surface of a recess of the printed circuit board, on which the measurement sensor is mounted, is formed at a different height from other portion of the printed circuit board in a thickness direction of the electronic device.

A height of the one surface of the recess may be lower than a height of the other portion.

The measurement sensor may be spaced apart from the other portion of the printed circuit board and may be positioned in a central portion of the recess.

A surface opposite the one surface of the recess of the printed circuit board may be formed at a different height from other portion of the printed circuit board in the thickness direction of the electronic device.

The printed circuit board may further include an insulation cap that shields a side of the measurement sensor and is positioned in the recess.

The insulation cap may be spaced apart from the other portion of the printed circuit board.

The insulation cap may include an insulating material.

The insulation cap may include silica aerogel.

The battery cover may include a lens positioned corresponding to the recess.

The lens may include a different material from other portion of the battery cover.

The lens may include a material transmitting infrared light.

The measurement sensor may include a first measurement sensor measuring a heart rate and a second measurement sensor measuring a body temperature. The lens may include a protrusion positioned corresponding to the second measurement sensor.

The protrusion may protrude toward the second measurement sensor.

The protrusion may protrude toward an outside of the electronic device.

The measurement sensor may include a first measurement sensor measuring a heart rate and a second measurement sensor measuring a body temperature.

The first measurement sensor and the second measurement sensor may be spaced apart from each other.

The second measurement sensor may include a thermopile converting infrared light into an electromotive force, and an amplifier spaced apart from the thermopile and amplifying the electromotive force.

The thermopile may be spaced apart from the battery cover.

Advantageous Effects

An effect of an electronic device according to the present disclosure is described as follows.

According to at least one aspect of the present disclosure, the present disclosure can more accurately measure a body temperature of a user because a recess of a printed circuit board, on which a measurement sensor is mounted, is thinner than other portion of the printed circuit board and is spaced apart from the other portion.

According to at least one aspect of the present disclosure, the present disclosure can concentrate infrared light on a second measurement sensor measuring a body temperature because a lens includes a protrusion positioned corresponding to the second measurement sensor.

Further scope of applicability of the present disclosure will become apparent from the detailed description given hereinafter. However, it should be understood that the detailed description and specific examples, while indicating preferred embodiments of the disclosure, are given by illustration only, since various changes and modifications within the spirit and scope of the disclosure will become apparent to those skilled in the art from this detailed description.

MODE FOR INVENTION

Reference will now be made in detail to embodiments of the disclosure, examples of which are illustrated in the accompanying drawings. Wherever possible, the same reference numbers will be used throughout the drawings to refer to the same or like parts. In general, a suffix such as "module" and "unit" may be used to refer to elements or components. Use of such a suffix herein is merely intended to facilitate description of the specification, and the suffix itself is not intended to give any special meaning or function. It will be noted that a detailed description of known arts will be omitted if it is determined that the detailed description of the known arts can obscure the embodiments of the disclosure. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Mobile terminals disclosed herein may be implemented using a variety of different types of devices. Examples of such devices include cellular phones, smart phones, laptop computers, digital broadcast terminals, personal digital assistants (PDAs), portable multimedia players (PMPs), navigators, slate computers (PCs), tablet PCs, ultra books, wearable devices (for example, smart watches, smart glasses, head mounted displays (HMDs)), and the like.

By way of non-limiting example only, further description will be made with reference to particular types of mobile terminals. However, such teachings may be equally applied to other types of mobile terminals, such as those types noted above. In addition, these teachings may also be applied to stationary terminals such as digital TV, desktop computers, digital signage, and the like.

Figure 1:
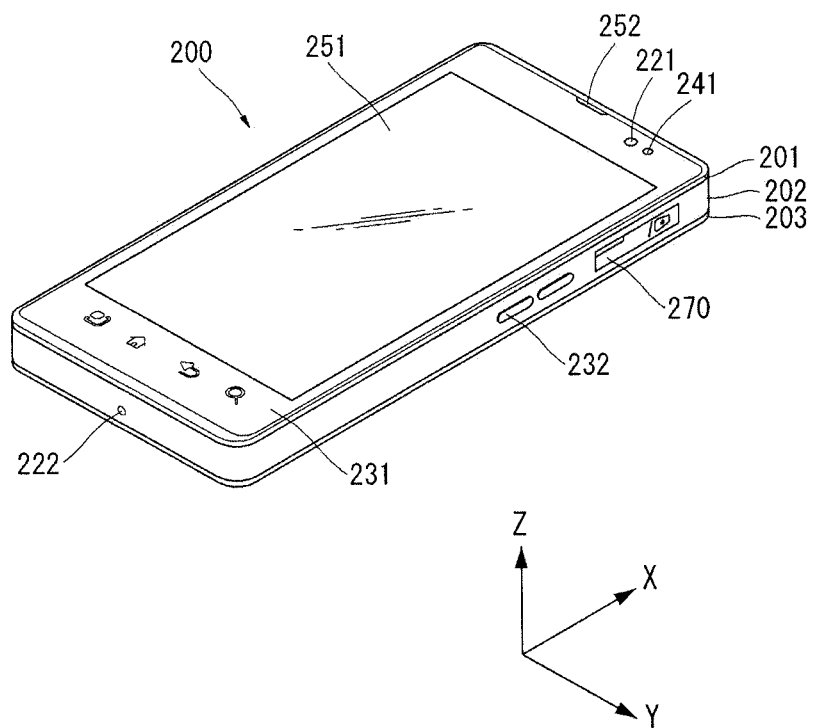
FIG. 1 is a perspective view of an example of a mobile terminal related to an embodiment of the disclosure when viewed from a front.
Figure 2:
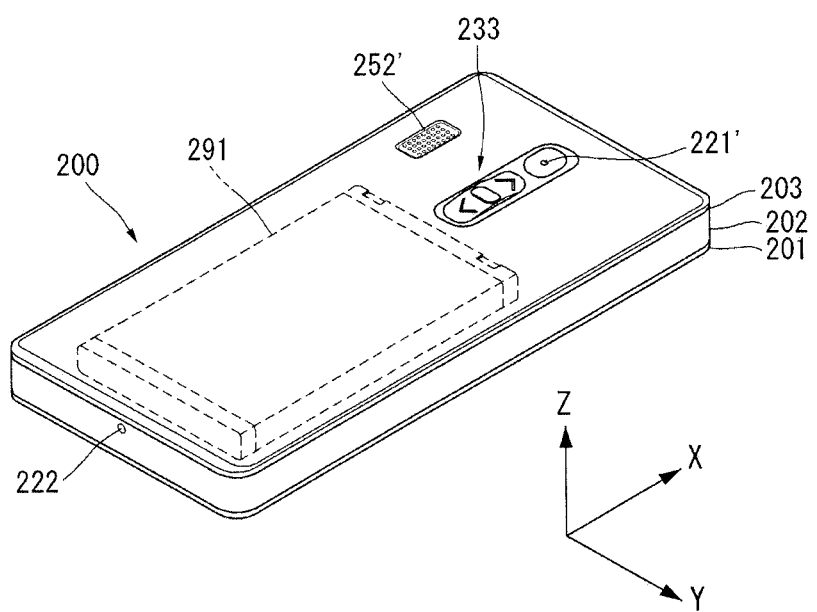
FIG. 2 is a rear perspective view of a mobile terminal shown in FIG. 1.

FIG. 1 is a perspective view of an example of a mobile terminal 200 related to an embodiment of the disclosure when viewed from a front. FIG. 2 is a rear perspective view of the mobile terminal 200 shown in FIG. 1.

The mobile terminal 200 has a terminal body of a bar shape. However, embodiments of the disclosure are not limited thereto. For example, embodiments of the disclosure may use various structures including a slide type in which two or more bodies are movably coupled to each other, a folder type, a swing type, a swivel type, etc.

The terminal body includes a case (including a casing, a housing, a cover, etc.) forming an appearance of the mobile terminal 200. In embodiments of the disclosure, the case may include a front case 201, a rear case 202, and a battery cover 203. Various elements are embedded in a space between the front case 201 and the rear case 202. At least one frame may be additionally disposed between the front case 201 and the rear case 202.

The cases may be formed by injection molding a synthetic resin. Alternatively, the cases may be formed using a metal material such as stainless steel (STS), titanium (Ti), and aluminum (Al).

A display unit 251, an audio output module 252, a proximity sensor 241, a camera module 221, and the like may be disposed on the terminal body, mainly the front case 201. A microphone 222, a side input unit 232, an interface 270, and the like may be disposed on the sides of the front case 201 and the rear case 202.

The display unit 251 occupies most of a main surface of the front case 201. Namely, the display unit 251 is disposed on a front surface of the terminal body and outputs visual information. The audio output module 252, the proximity sensor 241, and the camera module 221 may be disposed in an area adjacent to one end of both ends of the display unit 251, and a front input unit 231 may be disposed in an area adjacent to the other end of the display unit 251.

The front input unit 231 is an example of a user input unit and may include a plurality of manipulation units. The manipulation unit may also be commonly referred to as a manipulating portion. The manipulation unit may employ any tactile manner which is manipulated by a user while allowing the user to have a tactile feeling. In embodiments of the disclosure, the front input unit 231 is configured as a touch key. However, embodiments of the disclosure are not limited thereto, and a push key may be added to the front input unit 231.

The display unit 251 may form a touch screen together with a touch sensor. In this instance, the touch screen may be the user input unit. Hence, a configuration in which there is no the front input unit 231 on a front surface of the mobile terminal 200 may be used. In this instance, the mobile terminal 200 may be configured such that an input operation of the terminal body can be performed only through the display unit 251 and a rear input module 233 to be described later.

The side input unit 232 configured as another example of the user input unit can receive commands such as adjusting a volume of a sound output from a speaker 252' or a conversion to a touch recognition mode of the display unit 251.

Referring to FIG. 2, a camera module 221' may be additionally mounted on a rear surface of the terminal body, i.e., the rear case 202. The camera module 221' of the rear case 202 may be a camera that has a photographing direction substantially opposite to a photographing direction of the camera module 221 (see FIG. 1) of the front case 201 and has different pixels from the camera module 221 (see FIG. 1) of the front case 201.

For example, the front camera module 221 may have low pixels, so that the user can take a picture of his/her face with the front camera module 221 while making a video call and transmit it to the other party. The rear camera module 221' may have high pixels because it is often that the user takes pictures of general subjects with the rear camera module 221' and does not send them immediately. The camera modules 221 and 221' may be installed on the terminal body as rotatable or pop-up components.

A flash 223 and a mirror (not shown) may be additionally disposed adjacent to the camera module 221'. The flash 223 illuminates the subject when the subject is taken with the camera module 221'. When the user intends to take a picture (selfie-taking) of himself/herself using the camera module 221', the mirror can reflect his/her face, etc.

A speaker 252' may be additionally disposed on the rear surface of the terminal body. The rear speaker 252' can implement a stereo function together with the front speaker 252 (see FIG. 1). The rear speaker 252' may also be used to implement a speakerphone mode during a call.

A battery 291 is mounted on the terminal body to supply power to the mobile terminal 200. The battery 291 is configured as an example of a power supply unit. The battery 291 may be embedded in the terminal body or may be detachably attached to the terminal body.

As shown in FIG. 2, the rear input module 233 is disposed on the rear surface of the terminal body. The rear input module 233 is configured as another example of the user input unit. The rear input module 233 may be positioned adjacent to the camera module 221' exposed to the rear surface of the terminal body.

The rear input module 233 is manipulated to receive commands for controlling an operation of the mobile terminal 200. The commands may be set in a variety of different ways. For example, the rear input module 233 may receive a command such as power on/off, start, end, and scroll, a command of adjusting a volume of the sound output from the speakers 252 and 252', a command of the conversion to the touch recognition mode of the display unit 251, and the like.

The rear input module 233 according to the embodiment of the disclosure may be configured to permit a push input. Configuration of the rear input module 233 is described in detail below.

Figure 3:
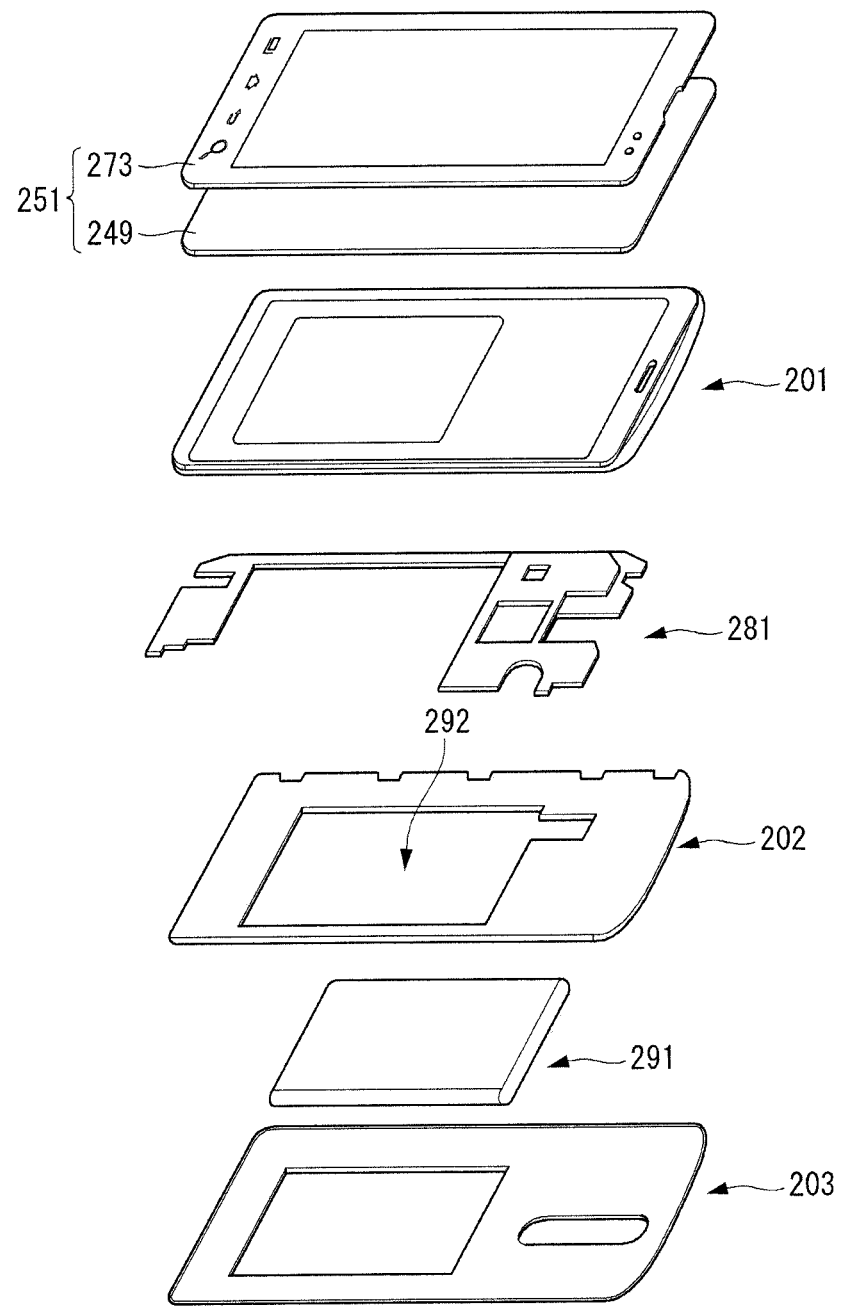
FIG. 3 is an exploded perspective view of a mobile terminal shown in FIG. 2.
Figure 4:
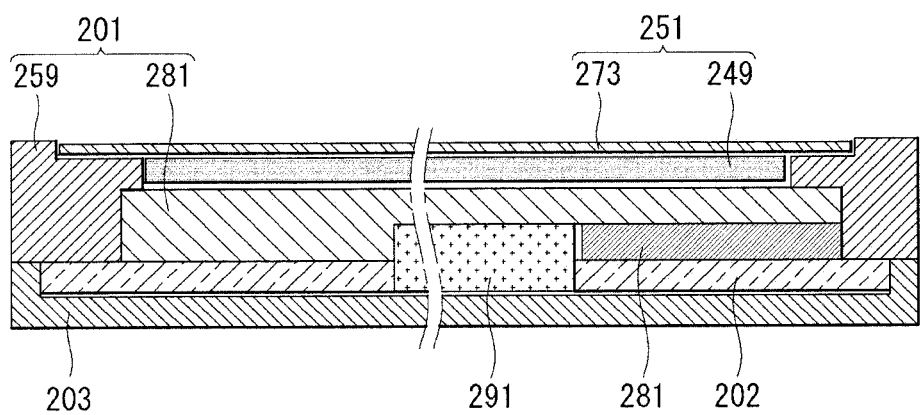
FIG. 4 is a cross-sectional view of a mobile terminal according to an embodiment of the disclosure.

FIG. 3 is an exploded perspective view of the mobile terminal 200 shown in FIG. 2. FIG. 4 is a cross-sectional view of the mobile terminal 200 according to the embodiment of the disclosure.

Referring to FIGS. 3 and 4, the display unit 251 of the mobile terminal 200 according to the embodiment of the disclosure may include a window glass 273 and a display module 249. The window glass 273 and the display module 249 may be formed as one body.

The window glass 273 may be coupled to one surface of the front case 201. A touch sensing pattern may be formed on one surface of the window glass 273 to sense a touch input. The touch sensing pattern may be configured to sense the touch input and may have light transmission characteristics. The touch sensing pattern may be positioned on a front surface or a rear surface of the window glass 273. The touch sensing pattern may convert changes in a voltage, etc. generated in a specific portion of the window glass 273 into an electrical input signal. The window glass 273 may include a transparent synthetic resin such as polycarbonate and acryl, or a glass material.

The display module 249 may be coupled to one surface of the window glass 273. For example, the display module 249 may be a thin film transistor liquid crystal display (TFT LCD). However, embodiments of the disclosure are not limited thereto. For example, the display module 249 may be a liquid crystal display, an organic light emitting diode (OLED) display, a flexible display, a three-dimensional (3D) display, and the like.

A printed circuit board 281 is embedded in the terminal body. The printed circuit board 281 may be mounted on the front case 201 or the rear case 202, or may be mounted on a separate structure. In the following description, embodiments of the disclosure are described using an example where the front case 201 and the rear case 202 are separately provided, but are not limited thereto. For example, the front case 201 and the rear case 202 may be formed as one body.

The printed circuit board 281 is configured as an example of a controller for operating various functions of the mobile terminal 200. The printed circuit board 281 includes various electronic elements mounted thereon, in order to perform functions of the controller. A plurality of printed circuit boards 281 is provided and can perform the functions of the controller through a combination of the printed circuit boards 281. For example, the printed circuit boards 281 include a main printed circuit board and a sub-printed circuit board that are electrically connected to each other. The printed circuit board 281 may be configured such that at least a portion of the main printed circuit board and at least a portion of the sub-printed circuit board are disposed to overlap each other in a thickness direction of the terminal body and thus may have a spatially extended structure.

The rear case 202 includes a battery accommodating portion 292 for accommodating the battery 291, and the battery cover 203 is detachably coupled to the rear case 202 to cover the battery accommodating portion 292. Unlike the above-described structure in which the battery 291 is detachable, the battery 291 may be embedded in the terminal body and cannot be detached.

The battery cover 203 is positioned on a rear surface of the display unit 251. At least a portion of the battery cover 203 may be formed of a metal material.

An edge portion and a central portion of the front case 201 may be formed of different materials. For example, the edge portion of the front case 201 may include a mold material, and the central portion of the front case 201 may include a metal material. As another example, the battery cover 203 may surround the sides of the electronic device 200. Namely, the battery cover 203 may be extended to the sides of the electronic device 200 and may cover the edge portion of the front case 201. As another example, the battery cover 203 may surround the sides of the electronic device 200, and the sides of the battery cover 203 may include a mold material.

Figure 5:
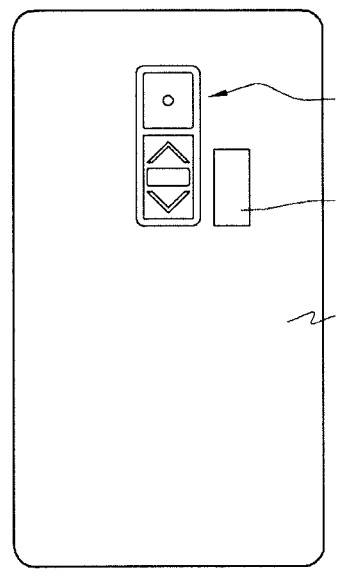
FIG. 5 is rear views of an electronic device according to an embodiment of the disclosure.
Figure 5:
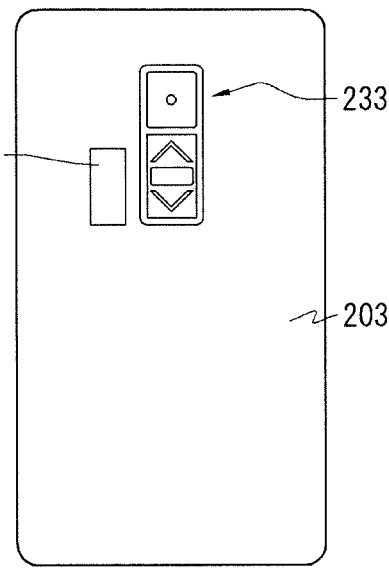
Figure 5:
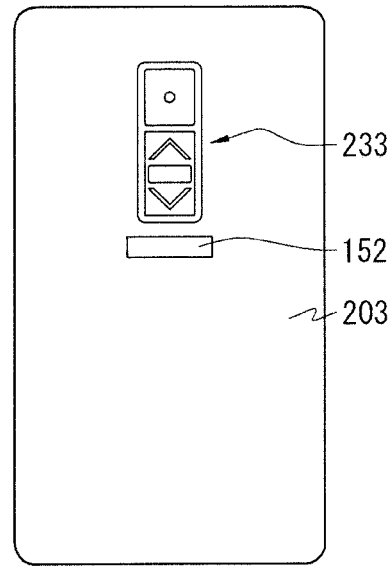
Figure 5:
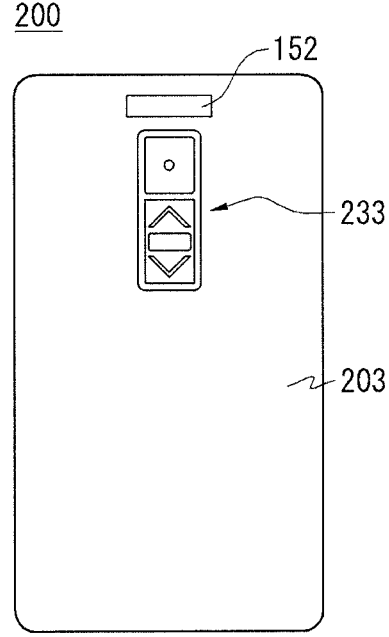

FIG. 5 is rear views of the electronic device according to the embodiment of the disclosure.

Referring to FIG. 5, in the electronic device 200 according to the embodiment of the disclosure, a measurement sensor 152 may be positioned on at least one side of the rear input module 233. The measurement sensor 152 may be spaced apart from the rear input module 233. For example, the measurement sensor 152 may be positioned on at least one side of the rear input module 233. As another example, the measurement sensor 152 may be positioned on an upper side or a lower side of the rear input module 233. Hence, the measurement sensor 152 and the rear input module 233 cannot be touched at the same time. The measurement sensor 152 may not be positioned in an edge portion of the battery cover 203 where an antenna circuit is positioned.

The measurement sensor 152 may be separated from a plurality of heat generating elements disposed therein. However, a position where the measurement sensor 152 is mounted may be limited due to the above-described antenna circuit or the like. Hence, the measurement sensor 152 may require a structure capable of minimizing an influence of heat generation even if it is adjacent to the heat generating element.

Figure 6:
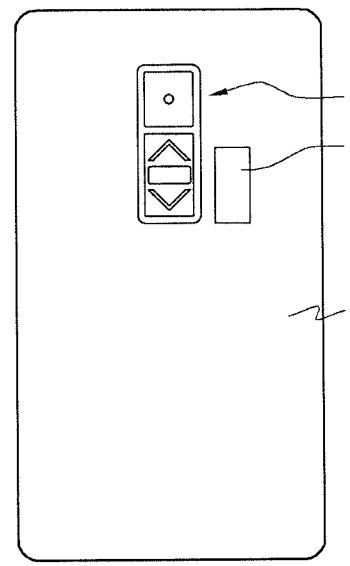
FIG. 6 is rear views illustrating an operation method of an electronic device according to an embodiment of the disclosure.
Figure 6:
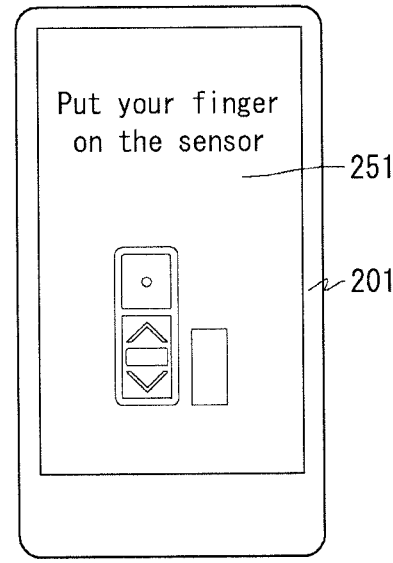
Figure 6:
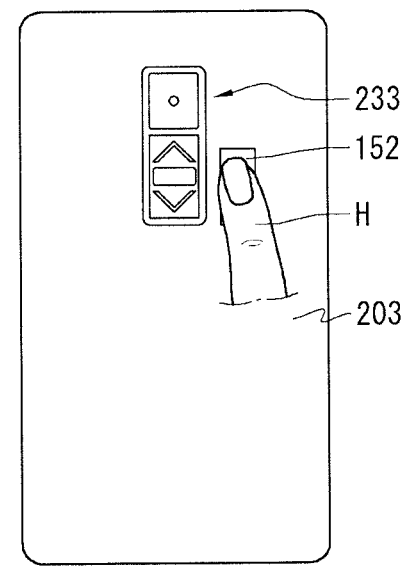
Figure 6:
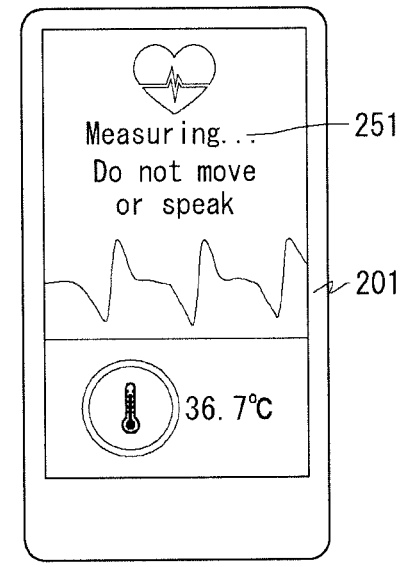

FIG. 6 is rear views illustrating an operation method of the electronic device according to the embodiment of the disclosure.

Referring to FIG. 6, in the electronic device 200 according to the embodiment of the disclosure, the controller may run an application for measuring a body temperature and a heart rate, in order to operate the measurement sensor 152. The controller may require a predetermined input for the measurement via the application. Namely, the controller may display a screen requiring the predetermined input on the display unit 251. For example, the predetermined input may be a long touch of a user's hand H on the measurement sensor 152.

When the predetermined input of the user is received, the controller may display the measured body temperature and/or heart rate of the user on the display unit 251. As shown in (b) of FIG. 6, the controller may display the body temperature of the user on one side of the display unit 251 and display the heart rate of the user on the other side of the display unit 251.

The electronic device 200 according to the embodiment of the disclosure can measure the body temperature and/or the heart rate of the user through a simple input. Hence, the user can more easily check his/her health condition.

Figure 7:
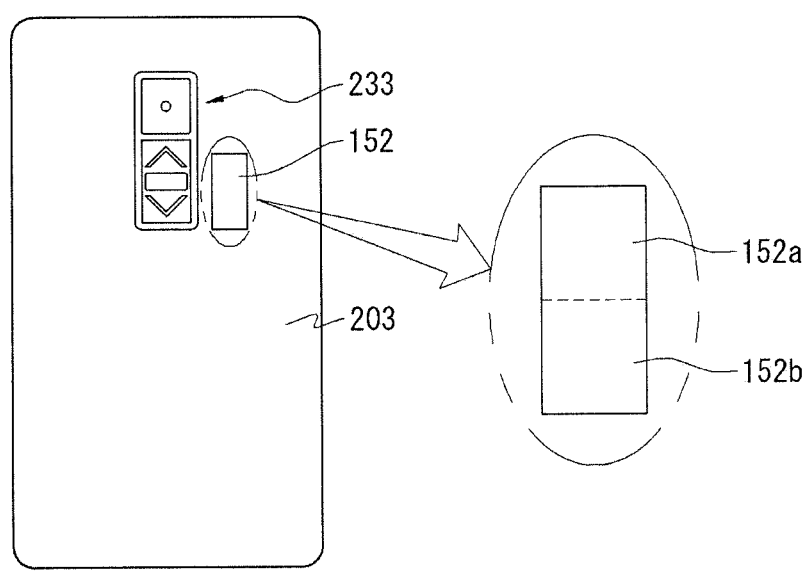
FIGS. 7 and 8 are rear views of an electronic device according to an embodiment of the disclosure.
Figure 8:
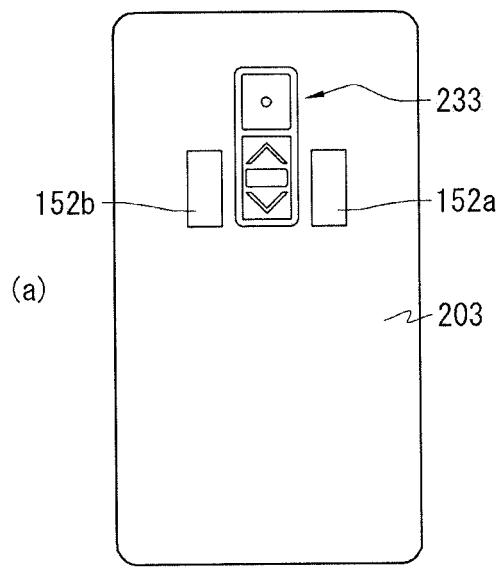
Figure 8:
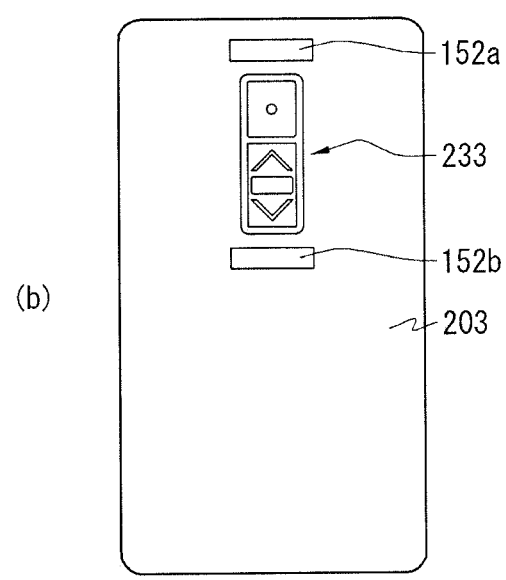

FIGS. 7 and 8 are rear views of the electronic device according to the embodiment of the disclosure.

Referring to FIG. 7, in the electronic device 200 according to the embodiment of the disclosure, the measurement sensor 152 may be divided into a plurality of areas. For example, the measurement sensor 152 may include a first measurement sensor 152a and a second measurement sensor 152b. When the measurement sensor 152 is divided into two parts, the first measurement sensor 152a may correspond to an upper part, and the second measurement sensor 152b may correspond to a lower part.

For example, the first measurement sensor 152a may be a sensor measuring a heart rate of the user, and the second measurement sensor 152b may be a sensor measuring a body temperature of the user. Hence, when the user touches the measurement sensor 152, the body temperature and/or the heart rate of the user can be measured at the same time. Because the measurement sensor 152 includes measurement sensors having various functions, various functions can be performed at a time.

FIGS. 7 and 8 illustrate only the first measurement sensor 152a and the second measurement sensor 152b, by way of example. However, embodiments of the disclosure are not limited thereto. The measurement sensor 152 may further include measurement sensors having other functions.

Referring to FIG. 8, in the electronic device 200 according to the embodiment of the disclosure, the first measurement sensor 152a and the second measurement sensor 152b may be spaced apart from each other.

For example, as shown in (a) of FIG. 8, the first measurement sensor 152a may be positioned to be spaced apart from the side of the rear input module 233, and the second measurement sensor 152b may be positioned opposite the first measurement sensor 152a with the rear input module 233 interposed therebetween.

As another example, as shown in (b) of FIG. 8, the first measurement sensor 152a may be positioned to be spaced apart from the upper part of the rear input module 233, and the second measurement sensor 152b may be positioned opposite the first measurement sensor 152a with the rear input module 233 interposed therebetween. Namely, the first and second measurement sensors 152a and 152b may be positioned at the upper part and the lower part of the rear input module 233.

Because the first measurement sensor 152a and the second measurement sensor 152b are spaced apart from each other and are positioned at different locations, the user can input a signal to only the measurement sensor he/she wants to use. Further, because the measurement sensors are spaced apart from each other, the measurement sensors cannot interfere with each other during the measurement.

FIG. 8 illustrates that the first and second measurement sensors 152a and 152b are positioned on the left and right sides or the upper and lower sides of the rear input module 233, by way of example. However, embodiments of the disclosure are not limited thereto. For example, the first and second measurement sensors 152a and 152b may be positioned to be spaced apart from each other in a portion not overlapping a portion on which an antenna is mounted.

Figure 9:
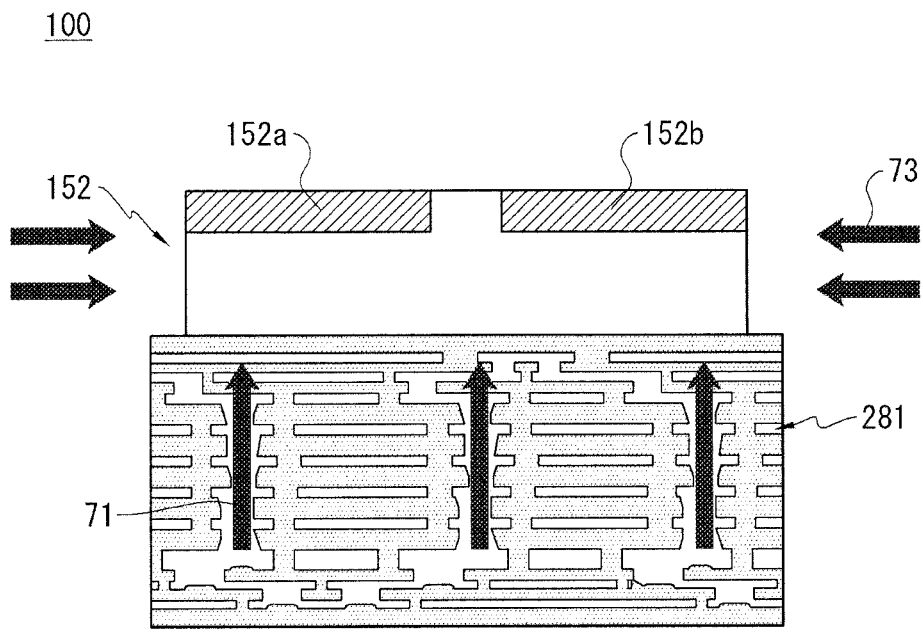
FIG. 9 is a cross-sectional view of an electronic device according to a related art.

FIG. 9 is a cross-sectional view of an electronic device according to a related art.

Referring to FIG. 9, in an electronic device 100 according to a related art, a measurement sensor 152 was positioned on a printed circuit board 281. Thus, conductive heat 71 was transferred from the printed circuit board 281 to the measurement sensor 152 on the printed circuit board 281. As a result, there was a problem that the measurement sensor 152 did not accurately measure a body temperature of the user.

Further, convective heat 73 emitted from another heat generating device might be transferred to the measurement sensor 152 through an air inside a case of the electronic device 100. Hence, there was a problem that the measurement sensor 152 did not accurately measure a body temperature of the user.

Sensors measuring a body temperature may be allowed to have an error within 0.2 degrees according to international standards. Thus, the conductive heat 71 or the convective heat 73 should not be transferred as much as possible. However, the related art electronic device 100 could not accurately measure the body temperature due to heat transferred from the printed circuit board 281.

Accordingly, the electronic device according to the embodiment of the disclosure requires a structure capable of preventing the conductive heat 71 and the convective heat 73 transferred to the measurement sensor 152.

FIGS. 10 to 20 illustrate an electronic device according to an embodiment of the disclosure.

Figure 10:
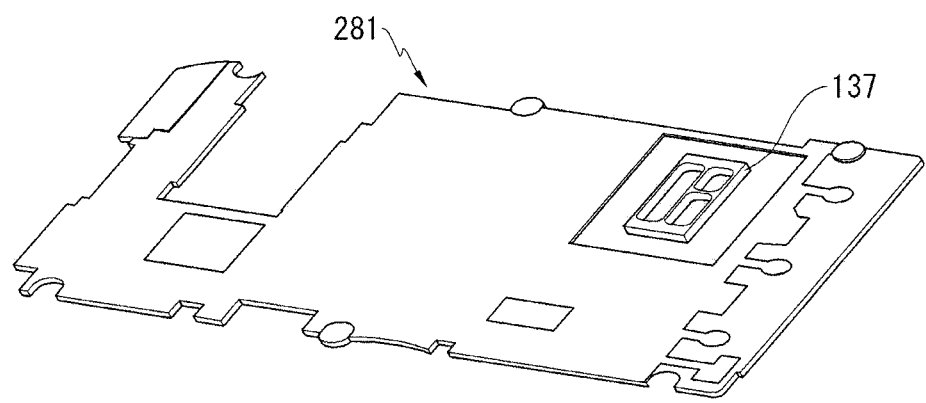
FIGS. 10 to 20 illustrate an electronic device according to an embodiment of the disclosure.
Figure 11:
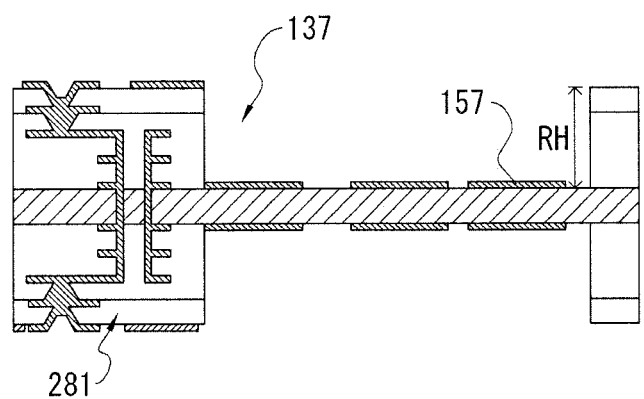

Referring to FIGS. 10 and 11, in the electronic device according to the embodiment of the disclosure, the measurement sensor 152 may be positioned in a recess 137 positioned in at least a portion of the printed circuit board 281. The recess 137 of the printed circuit board 281 may be depressed further than other portion of the printed circuit board 281 by a first height RH. A portion of the printed circuit board 281 where the measurement sensor 152 will be positioned may be etched to form the recess 137.

Any electric wire other than electric wires 157 directed to the measurement sensor 152 may not be positioned in the recess 137. Namely, when the printed circuit board 281 is formed, only the electric wires 157 for the measurement sensor 152 may be mounted in the recess 137, and another layer may not be deposited on the recess 137. Because other electric wires are not positioned in the recess 137, there is little conductive heat transferred to the measurement sensor 152. Further, a height of the measurement sensor 152 may be lower than a height of the printed circuit board 281.

The recess 137 may be positioned on both surfaces of the printed circuit board 281. Namely, both surfaces of the recess 137 of the printed circuit board 281 may have a groove. Both surfaces of the printed circuit board 281 may be etched twice to form the recess 137. Hence, the recess 137 of the printed circuit board 281 may have a thickness much smaller than other portion.

The thickness of the recess 137 is less than a thickness of other portion, and the electric wires 157 are disposed less in the recess 137 than the other portion. Therefore, heat transferred to the measurement sensor 152 can greatly decrease. Hence, when a body temperature of the user is measured using the measurement sensor 152, an error can decrease.

Figure 12:
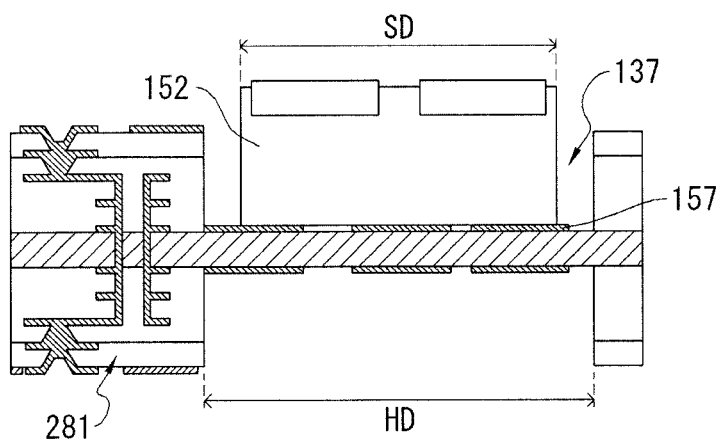

Referring to FIG. 12, the measurement sensor 152 may be mounted in the recess 137. The measurement sensor 152 may be positioned in the center of the recess 137. A width SD of the measurement sensor 152 may be less than a width HD of the recess 137. Hence, the measurement sensor 152 may not contact other portion of the printed circuit board 281. Namely, the side of the measurement sensor 152 may be spaced apart from the side of the other portion of the printed circuit board 281.

Because the electric wires 157 are disposed less in a lower surface of the measurement sensor 152 than other portion of the printed circuit board 281, less heat may be transferred to the measurement sensor 152. Further, because the side of the measurement sensor 152 is spaced apart from the side of the other portion of the printed circuit board 281, conductive heat may not be transferred to the measurement sensor 152. Hence, even if a light emitting element is positioned on the printed circuit board 281 around the measurement sensor 152, an influence of the light emitting element on the measurement sensor 152 can be reduced.

FIG. 12 illustrates that a height of an upper surface of the measurement sensor 152 is higher than a height of an upper surface of other portion of the printed circuit board 281, by way of example. In this instance, because the measurement sensor 152 protrudes from the printed circuit board 281, the measurement sensor 152 may be advantageous to heat dissipation. However, embodiments of the disclosure are not limited thereto. For example, a height of the upper surface of the measurement sensor 152 may be lower than a height of the upper surface of the other portion of the printed circuit board 281. In this instance, because the measurement sensor 152 does not protrude from the printed circuit board 281, an inner space of the electronic device can be saved.

Figure 13:
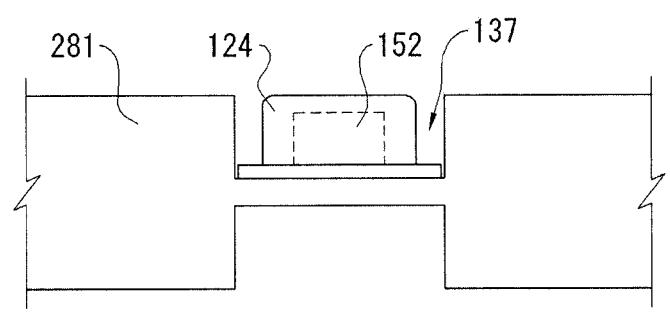
Figure 13:
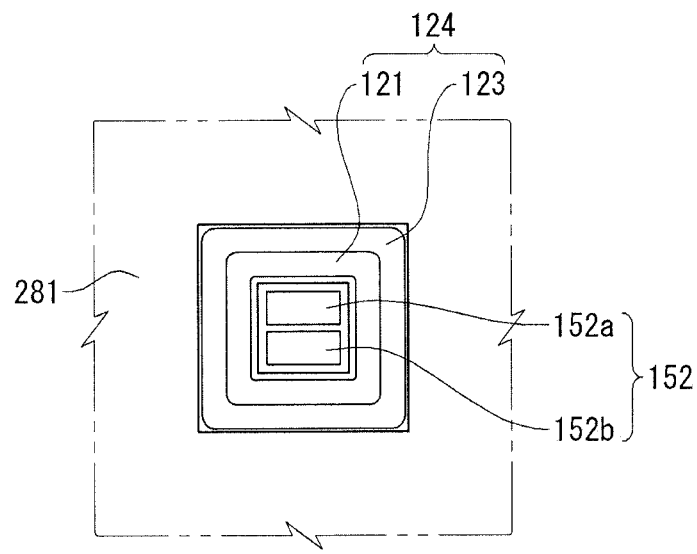

Referring to FIG. 13, in the electronic device according to the embodiment of the disclosure, an insulation cap 124 for shielding the measurement sensor 152 may be positioned on the side of the measurement sensor 152. The insulation cap 124 may include an insulating material. For example, the insulation cap 124 may include silica aerogel. The insulation cap 124 may surround the side of the measurement sensor 152.

The insulation cap 124 may not be filled in the entire area of the recess 137. Namely, the insulation cap 124 may be spaced apart from other portion of the printed circuit board 281. Hence, the insulation cap 124 does not transfer conductive heat to the measurement sensor 152 and can block convective heat.

The insulation cap 124 does not shield the upper surface of the measurement sensor 152 and may shield only the side of the measurement sensor 152 for the measurement. The insulation cap 124 may be spread flat on the bottom of the recess 137, in order to support four sides of the measurement sensor 152.

Figure 14:
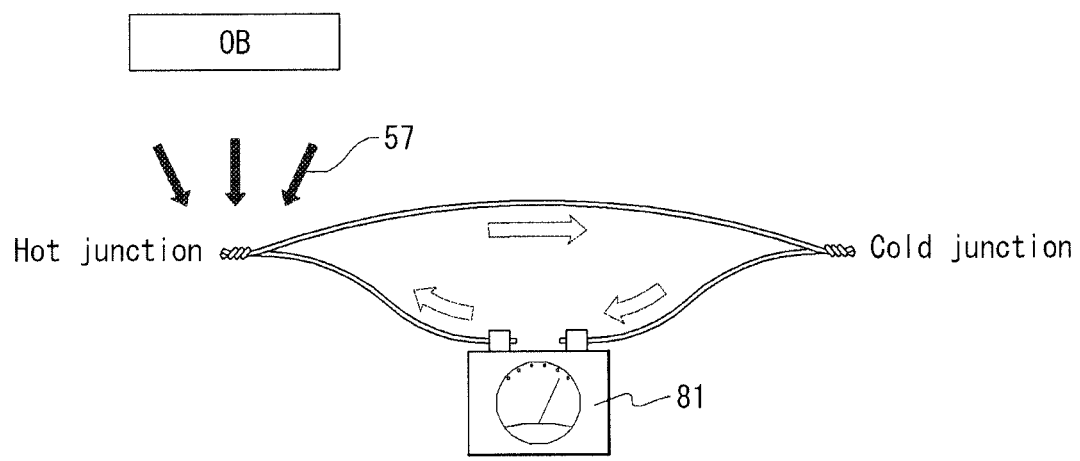

Referring to FIG. 14, in the electronic device according to the embodiment of the disclosure, a body temperature can be measured using infrared light 57 emitted from an object OB. Two different metals or two different semiconductors inside a body temperature measuring sensor may be connected to each other. Namely, both ends of the two different metals or both ends of the two different semiconductors may be connected to each other. The infrared light 57 emitted from the object OB may be radiated onto one of both connection points of the two different metals or the two different semiconductors, and a temperature of the one connection point may increase. Namely, radiant energy of the infrared light 57 emitted from the object OB is converted into thermal energy. When a temperature of one connection point is higher than a temperature of the other connection point, an electromotive force may be generated in a circuit formed by connecting the two metals or the two semiconductors. Namely, the thermal energy is converted into electric energy.

Hence, the body temperature can be measured using a voltage measured by a voltmeter 81 of the circuit. The above-described principle may be referred to seebeck effect.

The infrared light 57 emitted from the object OB may be a band of far infrared light emitted from the human body. Hence, the body temperature measuring sensor may include a layer for easily absorbing the far infrared light band.

Figure 15:
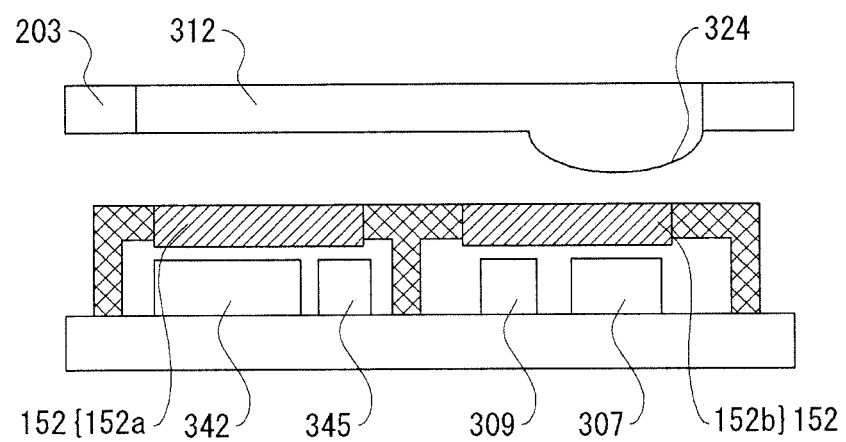

Referring to FIG. 15, in the electronic device according to the embodiment of the disclosure, a lens 312 may be positioned on the measurement sensor 152. The lens 312 may be positioned on the battery cover 203 at a location corresponding to the measurement sensor 152.

The lens 312 may transfer the infrared light 57 emitted from the object OB to the measurement sensor 152. Hence, the lens 312 can transmit the infrared light 57. For example, the lens 312 may include one of glass, plastic, germanium, silicon, and a combination thereof.

At least a portion of the lens 312 may protrude. More specifically, the lens 312 may include a protrusion 324 that protrudes toward the measurement sensor 152. The protrusion 324 may be positioned in an area corresponding to a second measurement sensor 152$b$ serving as the body temperature measuring sensor.

The protrusion 324 may serve as a convex lens that is configured such that a central portion is thicker than other portion. Hence, the protrusion 324 may allow the infrared light 57 emitted from the object OB to be directed toward the second measurement sensor 152$b$. Namely, the protrusion 324 can make the second measurement sensor 152$b$ work better.

A first measurement sensor 152$a$ may be a heart rate measurement sensor. A photodiode 342 and a light source 345 may be positioned inside the first measurement sensor 152$a$. The photodiode 342 and the light source 345 may be positioned to be spaced apart from each other. A method for driving the first measurement sensor 152$a$ will be described in detail later.

A thermopile 307 and an amplifier 309 may be positioned inside the second measurement sensor 152b. A method for driving the second measurement sensor 152b will be described in detail later.

The electronic device according to the embodiment of the disclosure can collect the infrared light 57 of the object OB to the measurement sensor 152 because at least a portion of the lens 312 protrudes. Hence, the second measurement sensor 152b can operate better.

Figure 16:
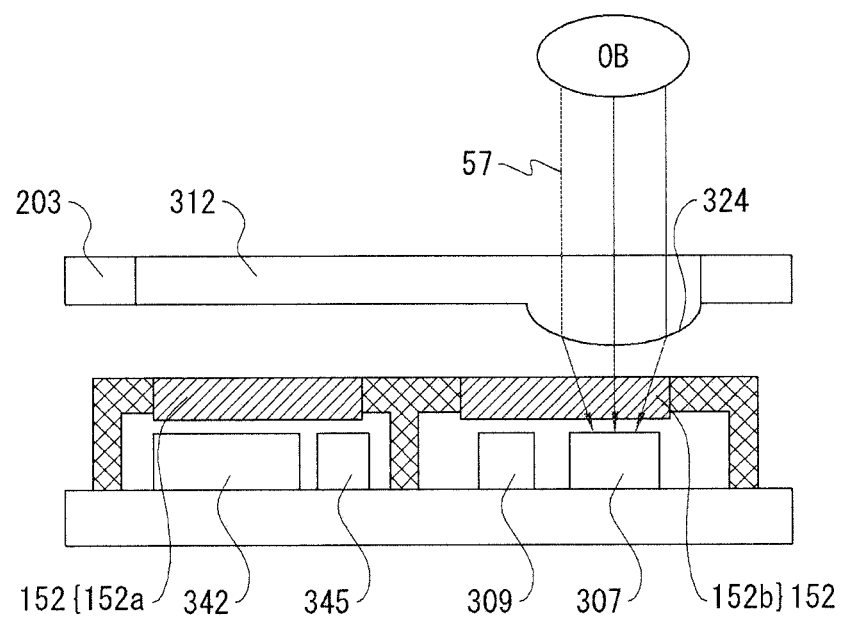

Referring to FIG. 16, in the electronic device according to the embodiment of the disclosure, the thermopile 307 may absorb the infrared light 57 of the object OB through the protrusion 324. Because the infrared light 57 is concentrated on the thermopile 307, the second measurement sensor 152b can operate better.

The infrared light 57 directed to the thermopile 307 may generate an electromotive force due to the above-described seebeck effect. A signal of the electromotive force generated in the thermopile 307 may be weak. Hence, the amplifier 309 may be positioned adjacent to the thermopile 307 so that the amplifier 309 amplifies the signal. As the amplifier 309 amplifies the signal, an intensity of the signal may increase compared to a noise. Hence, the body temperature can be measured more accurately.

Figure 17:
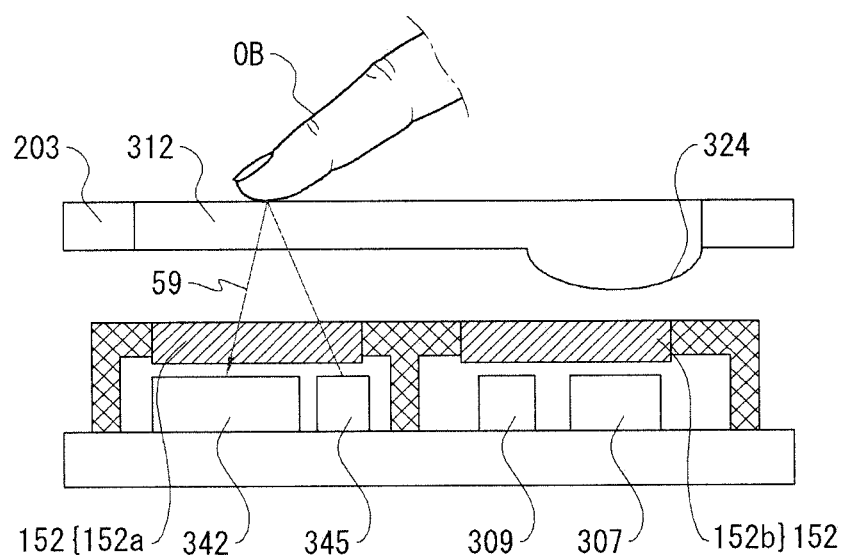

Referring to FIG. 17, in the electronic device according to the embodiment of the disclosure, light 59 emitted from the light source 345 may pass through the object OB and may be diffused, and a portion of the light 59 may be reflected.

In this instance, an amount of the light 59 reflected to the photodiode 342 may change depending on the contraction and the relaxation of the heart. For example, when the heart contracts, the object OB may be filled with blood and may become dark, and an amount of the light 59 reflected to the photodiode 342 may decrease. On the contrary, when the heart relaxes, blood may be removed from the object OB, and the object OB may be brightened. Further, an amount of the light 59 reflected to the photodiode 342 may increase.

Hence, the first measurement sensor 152a can measure a heart rate by measuring change in a brightness.

The light 59 emitted from the light source 345 may pass through the object OB without the refraction and may be directed toward the photodiode 342. Hence, the light source 345 and the photodiode 342 can serve as a transmission module and a reception module. Further, a portion of the lens 312 corresponding to the first measurement sensor 152a may be flat, in order to perform transmission and reception operations without the refraction.

Figure 18:
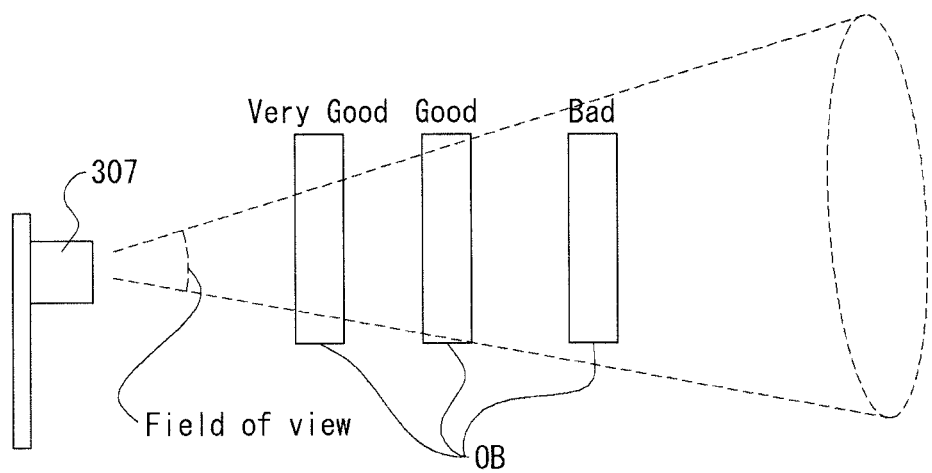

Referring to FIG. 18, the electronic device according to the embodiment of the disclosure can perform the measurement more accurately when the object OB is positioned within a field of view of the thermopile 307. When at least a portion of the object OB is positioned out of the field of view of the thermopile 307, the accurate measurement cannot be performed. Hence, as a distance between the object OB and the thermopile 307 decreases, the object OB is positioned within the field of view of the thermopile 307. As a result, the measurement can be performed more accurately.

However, when the thermopile 307 contacts the object OB, it affects a thermal equilibrium state of the thermopile 307. It may be difficult to accurately measure the body temperature. When the thermopile 307 is spaced apart from the object OB, the body temperature can be measured more accurately. Namely, the battery cover 203 may be spaced apart from the thermopile 307.

Thus, even if the thermopile 307 and the object OB are spaced apart from each other, the above-described protrusion 324 (see FIG. 16) may be used to perform the accurate measurement so that the object OB is easily positioned within the field of view of the thermopile 307.

Figure 19:
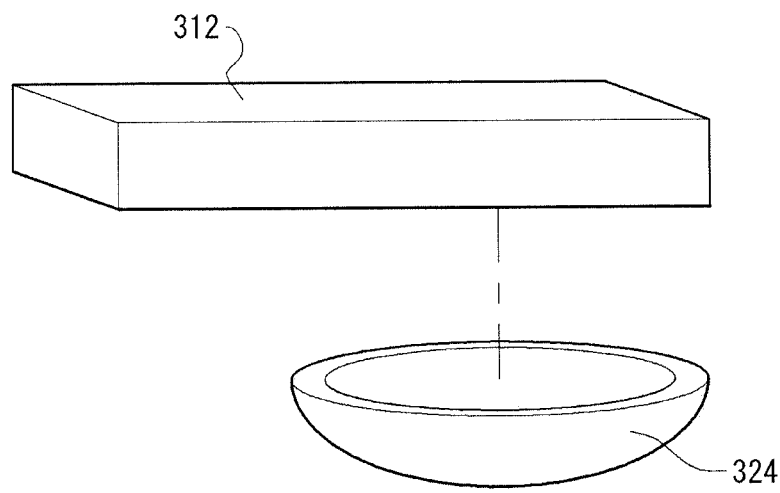

Referring to FIG. 19, in the electronic device according to the embodiment of the disclosure, the protrusion 324 may be attached to at least a portion of the lens 312. The protrusion 324 may be attached to the lens 312 using an UV bonding method or an adhesive layer. The protrusion 324 may be attached to a flat lower surface of the lens 312 at a location corresponding to the second measurement sensor 152b (see FIG. 17).

The protrusion 324 may include the same material as the lens 312 and may serve as a convex lens that is configured such that a central portion is thicker than other portion. Hence, the protrusion 324 can collect light directed to the lens 312 to the central portion of the protrusion 324. FIG. 19 illustrates that the central portion of the protrusion 324 is empty, by way of example. However, embodiments of the disclosure are not limited thereto. For example, the inside of the protrusion 324 may be filled.

Figure 20:
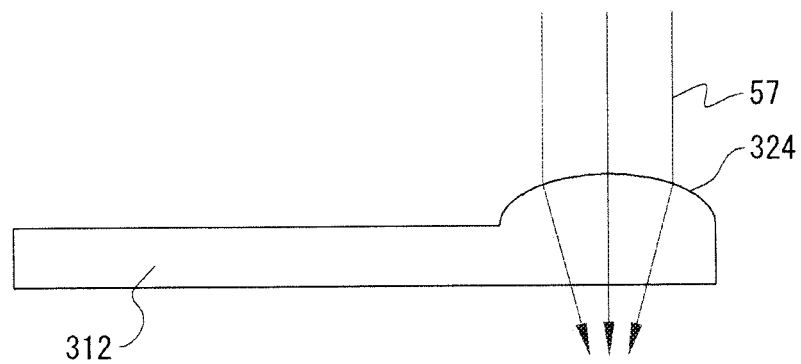

Referring to FIG. 20, in the electronic device according to the embodiment of the disclosure, the protrusion 324 may protrude toward the opposite direction of the measurement sensor. Namely, when the lens 312 is assembled to the electronic device, the protrusion 324 may be exposed to the outside.

Even if a protruding direction of the protrusion 324 is the opposite direction of the measurement sensor, the protrusion 324 can equally perform a function of collecting the infrared light 57. Namely, because the central portion of the protrusion 324 is thicker than other portion, the protrusion 324 can allow the infrared light 57 emitted to other portion to be emitted toward the central portion of the protrusion 324.

When the protrusion 324 is exposed to the outside, the user can easily sense a position of the lens 312. Hence, the user can find more easily a location to measure the body temperature and/or the heart rate. In particular, the measurement sensor may be positioned in the battery case of the rear surface of the electronic device. Hence, the user can measure more easily the body temperature and/or the heart rate while seeing a display screen without looking at the rear surface of the electronic device.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller of the terminal.

The foregoing embodiments are merely examples and are not to be considered as limiting the present disclosure. The present teachings can be readily applied to other types of methods and apparatuses. The features, structures, methods, and other characteristics of the embodiments described herein may be combined in various ways to obtain additional and/or alternative embodiments.

The invention claimed is:

1. An electronic device comprising:
a case having a surface and providing an inner space;

a printed circuit board (PCB) in the case, the PCB facing the surface and spaced apart from the surface, and the PCB having a first side and a second side facing each other;

a measurement sensor positioned between the surface and the PCB and mounted on the PCB; and an insulating wall extending along a periphery of the measurement sensor, coupled to the PCB and adjacent the measurement sensor, wherein the PCB includes a recess, and a gap between the first side and the second side in the recess is smaller than the gap between the first side and the second side area excluding the recess, wherein a plurality wires are mounted in the PCB, and among the plurality wires only wires connected to the measurement sensor are mounted in the recess, wherein the measurement sensor is positioned in the recess, wherein the case includes a lens positioned corresponding to the measurement sensor in the form of a convex lens, and wherein the measurement sensor includes:

a first measurement sensor measuring a heart rate; and a second measurement sensor measuring a body temperature, and wherein the lens includes a protrusion positioned corresponding to the second measurement sensor.

2. The electronic device of claim 1, wherein a height of the insulating wall is higher than a height of the measurement sensor.

3. The electronic device of claim 1, further comprising a battery cover covering the surface of the case.

4. The electronic device of claim 1, wherein the measurement sensor is spaced apart from the other portion of the PCB and is positioned in a central portion of the recess.

5. The electronic device of claim 4, wherein the insulating wall is spaced apart from the other portion of the PCB.

6. The electronic device of claim 1, wherein the insulating wall includes a through hole, and wherein the measurement sensor is positioned in the through hole.

7. The electronic device of claim 1, wherein the insulating wall is positioned in the recess.

8. The electronic device of claim 1, wherein the insulating wall includes an insulating material.

9. The electronic device of claim 1, wherein the insulating wall includes silica aerogel.

10. The electronic device of claim 1, wherein the lens includes a different material from another portion of the case.

11. The electronic device of claim 1, wherein the lens includes a material transmitting infrared light.

12. The electronic device of claim 1, wherein the protrusion protrudes toward the second measurement sensor.

13. The electronic device of claim 1, wherein the protrusion protrudes toward an outside of the electronic device.

14. The electronic device of claim 1, wherein the first measurement sensor and the second measurement sensor are spaced apart from each other.

15. The electronic device of claim 1, wherein the second measurement sensor includes:

a thermopile converting infrared light into an electromotive force; and an amplifier spaced apart from the thermopile and amplifying the electromotive force.

16. The electronic device of claim 15, wherein the thermopile is spaced apart from the case.

* * * * *